May 28, 1974 R. E. HOLDREN Plant Pat. 3,558
APPLE TREE
Filed Jan. 15, 1973
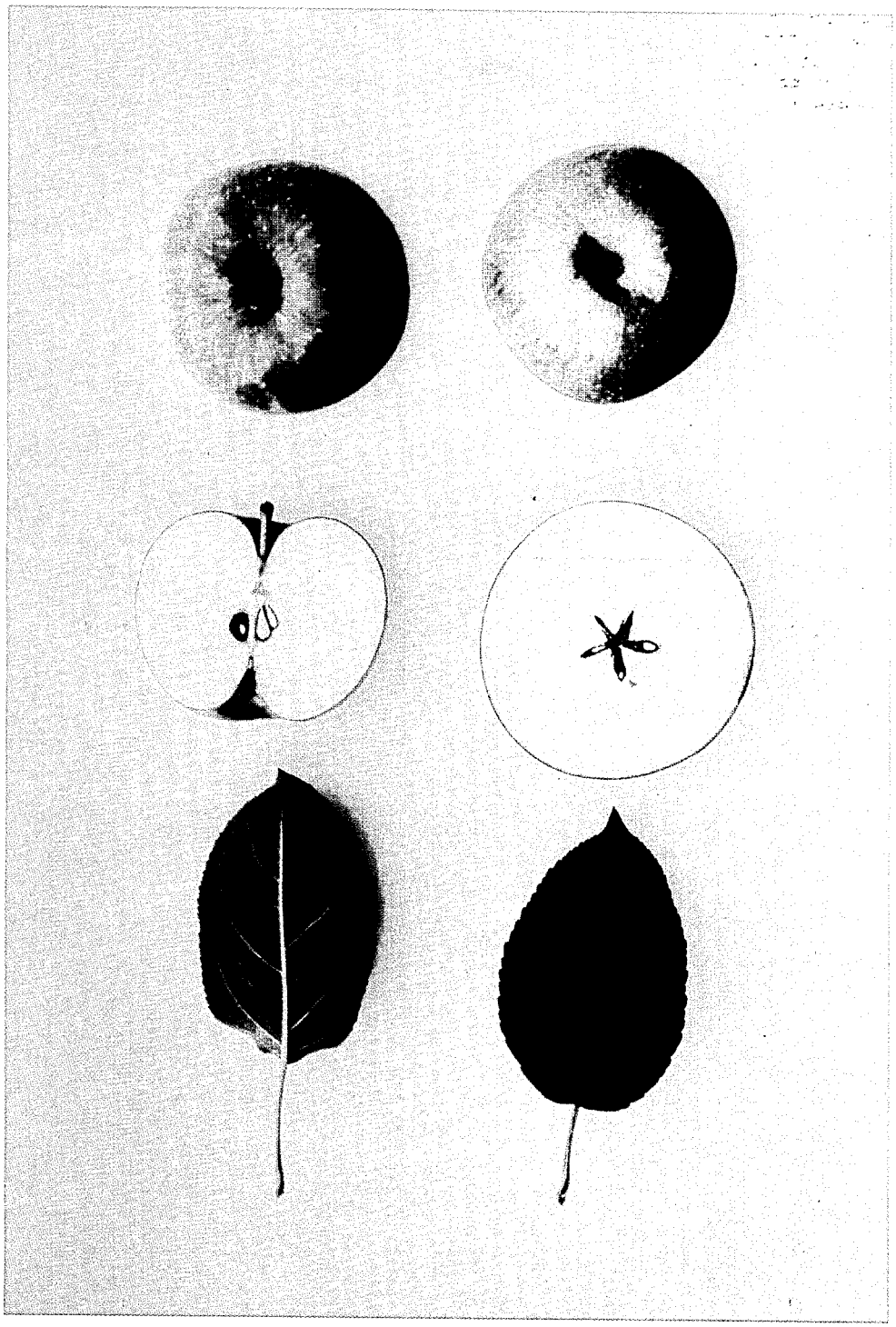

United States Patent Office

Plant Pat. 3,558
Patented May 28, 1974

3,558
APPLE TREE

Robert E. Holdren, Little Hocking, Ohio 45742

Filed Jan. 15, 1973, Ser. No. 323,805
Int. Cl. A01h *5/03*
U.S. Cl. Plt.—34 1 Claim The present invention relates to a new and distinct variety of apple tree which was originated by me by crossing an unnamed and unpatented seedling of the apple variety known as "Rome Beauty" (unpatented) with an unnamed and unpatented seedling of the apple variety known as "Wealthy" (unpatented), the former being the male parent and the latter being the female parent.

This cross was a part of a breeding program conducted by me in my commercial orchards located at Little Hocking, Ohio, in an effort to produce and develop a new and improved firm summer apple variety which bears fruit that is capable of withstanding grading, shipping and other handling better than other standard varieties heretofore available in commerce. This objective was fully achieved by me, among other improvements, as evidenced by the following unique combination of characteristics which are outstanding in my new variety, and which distinguish it from its parents, as well as from all other apple varieties of which I am aware:

(1) A vigorous, hardy, upright, medium tall and dense habit of growth, with strong and well-crotched limbs;
(2) An early and regular fruit-bearing habit, with the fruit reaching full color and maturity about August first in Ohio (about three weeks earlier than the fruit of "Wealthy" which it generally resembles);
(3) A distinctive and attractive bright red and waxy fruit color, with a greenish scarfskin;
(4) Crisp, juicy, slightly tart fruit flesh which makes the fruit excellent for both eating and cooking; and
(5) A fruit firmness comparable to that of "Rome Beauty," with consequent good keeping, handling and shipping qualities.

Asexual reproduction of my new variety, as performed by me by buddings in my orchards at Little Hocking, Ohio, shows that the foregoing characteristics and distinctions come true to form and are established and transmitted through succeeding propagations.

The accompanying drawing shows typical specimens of the foliage and fruit of my new apple variety, as depicted in color as nearly true as it is reasonably possible to make the same in a color illustration of this character, said fruit being shown in both top and bottom plan, as well as in both longitudinal and transverse cross-section, and the foliage specimens depicting both the upper and under surfaces of typical leaves.

The following is a detailed description of the new variety, with color terminology in accordance with Maerz and Paul Dictionary of Color, except where general color terms of ordinary dictionary significance are obvious:

Breeding: Seedling.
*Male parent.*—"Rome Beauty."
*Female parent.*—"Wealthy."
Propagation: Holds its distinguishing characteristics through succeeding propagations by budding.
Locality where grown and observed: Little Hocking, Ohio.
Dates of first and last pickings: About July 28 and August 10, respectively, depending on seasonal conditions.
Tree: Medium size; vigorous; upright; medium tall; dense; round-topped; hardy; productive; regular bearer.
*Trunk.*—Medium caliper; smooth.

*Branches.*—Medium thickness; smooth; much branched. Color.—Gray-brown, Plate 15–E–5. Lenticels—Medium number; large.
*Leaves.*—Medium size; medium length; medium width; oval; abruptly pointed; mucronate; medium thickness. Lengthy—About 3½ inches. Width—About 2⅛ inches. Upper surface—Smooth; color—Dark green. Under surface—Rugose; color—Light green. Margin—Crenate. Petiole—Long (about 1½ inches); medium thickness.
Flowers:
*First bloom.*—From about April 20 to April 25, depending on seasonal conditions.
*Full bloom.*—From about 5 days to 1 week after first bloom; about the same as "Wealthy," "Delicious," "Grimes Golden" or "Stayman" varieties.
*Size.*—About the same size as "Rome Beauty."
*Color.*—White, with a slight amount of red or pink toward base of petals.
Fruit:
*Maturity when described.*—Eating hard; about August 1st to 10th.
*Size.*—Uniform. Axial diameter—About 2¾ inches. Transverse diameter—About 3 inches.
*Form.*—Uniform; unsymmetrical; compressed laterally; oblate.
*Cavity.*—Symmetrical; abrupt at base; acute; undulate; pubescent toward apex. Depth—From about ½ inch to ⅝ inch. Breadth—About ½ inch. Markings—Greenish scrafskin.
*Basin.*—Unsymmetrical; rounded; narrow-base; undulate; pubsecent.
*Stem.*—Medium caliper; pubescent. Length—About 11/16 inch. Bracts—Present (1 or 2).
*Calyx.*—Closed; segments persistent; broadly lanceoleate; acuminate; about ¼ inch long; imbricate at based; erect reflexed at apex; convient. Outer surface—Pubescent. Inner surface—Pubescent.
*Eye.*—Small; closed.
*Skin.*—Thick; tough; smooth; glossy; waxy. Dots—Conspicuous; many; small; even; circular. Color—White. Distribution—Heavy toward calyx and slight toward stem. Ground color—Creamy yellow, Plate 10–I–2. Color markings—Blushed; bright; with faint stripe; color—Bright red, Plate 4–L–5. Bloom—Wanting. Scarfskin—Light; slight distribution; color—Greenish.
Flesh:
*Color.*—Cream, Plate 9–B–1.
*Texture.*—Firm; fine; crisp.
*Flavor.*—Subacid; delicate.
*Aroma.*—Distinct.
*Quality.*—Good.
Core: Median.
*Bundle area.*—Cordate; symmetrical.
*Halves of core area.*—Equal.
*Bundles.*—Conspicuous; color—Greenish yellow, Plate 18–I–6.
*Alternate bundle.*—Distant from calyx-tube, but reaches tube at stamens.
*Core lines.*—Clasping.
*Cross section.*—Distinct.
*Carpellary area.*—Large.
*Calyx-tube.*—Pubescent toward base; funnel form. Stem of funnel—short; depth of tube to shoulder—about ⅜ inch; entire depth—about ⅝ inch.
*Styles.*—Present; distinct; pubescent toward base.
*Stamens.*—In one basal whorl.
*Axillary cavity.*—Wanting.

*Seed cells.*—Axile; closed. Cell walls—Approximate; thick; tough. Length—About 9/16 inch. Breadth—About 3/8 inch. Longitudinal section—Broadly oval. Surface—Tufted. Cross section—Narrow.

Seeds: Usually 10 and all perfect; not more than 2 seeds per cell.

*Length.*—About 3/8 inch.

*Breadth.*—About 3/16 inch.

*Form.*—Acuminate.

*Color.*—Caldera, Plate 7–A–12.

Use: Local dessert; culinary.

Keeping quality: Very good; from about 200 to 220 days in regular cold storage at temperature of about 33° F.

Insect and disease resistance: Good resistance to usual apple insects and diseases, and particularly not susceptible to scab, as determined by comparison with other apple varieties grown under the same conditions at Litttle Hocking, Ohio.

I claim:

1. A new and distinct variety of apple tree, substantially as herein shown and described, characterized particularly as to novelty by the unique combination of a vigorous, hardy, upright, medium tall and dense habit of growth, with strong and well-crotched limbs, an early and regular fruit-bearing habit, with the fruit reaching full color and maturity about August first in Ohio (about three weeks earlier than the fruit of "Wealthy" which it generally resembles), a distinctive and attractive bright red and waxy fruit color with a greenish scarfskin, crisp, juicy, slightly tart fruit flesh which makes the fruit excellent for both eating and cooking, and a fruit firmness comparable to that of "Rome Beauty," with consequent good keeping, handling and shipping qualities.

No references cited.

ROBERT E. BAGWILL, Primary Examiner